US007872158B2

(12) United States Patent
Peterson et al.

(10) Patent No.: US 7,872,158 B2
(45) Date of Patent: *Jan. 18, 2011

(54) CHEMICAL PRODUCTION PROCESSES, SYSTEMS, AND CATALYST COMPOSITIONS

(75) Inventors: Thomas H. Peterson, Midland, MI (US); Alan H. Zacher, Pasco, WA (US); Michel J. Gray, Pasco, WA (US); James F. White, Richland, WA (US); Todd A. Werpy, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/895,414

(22) Filed: Aug. 24, 2007

(65) Prior Publication Data

US 2009/0054695 A1 Feb. 26, 2009

(51) Int. Cl.
*C07C 45/51* (2006.01)
*C07C 45/52* (2006.01)

(52) U.S. Cl. .................. 568/485; 568/403; 568/406; 568/486; 568/489

(58) Field of Classification Search .......... 568/403, 568/406, 485, 489; 502/174, 217, 240, 243, 502/263, 355
See application file for complete search history.

(56) References Cited

U.S. PATENT DOCUMENTS

| 2,516,627 | A |   | 7/1950  | Hearne et al. |         |
|-----------|---|---|---------|---------------|---------|
| 2,558,520 | A |   | 6/1951  | Hoyt et al.   |         |
| 3,197,483 | A | * | 7/1965  | Buchholz et al. | 549/83 |
| 3,893,946 | A |   | 7/1975  | Weisang et al. |        |
| 4,137,271 | A | * | 1/1979  | Stiles et al. | 568/471 |
| 4,234,752 | A |   | 11/1980 | Wu et al.     |         |
| 4,642,394 | A | * | 2/1987  | Che           | 568/861 |
| 4,729,978 | A |   | 3/1988  | Sawicki       |         |
| 5,387,720 | A |   | 2/1995  | Neher et al.  |         |
| 5,426,249 | A |   | 6/1995  | Haas et al.   |         |
| 5,753,716 | A |   | 5/1998  | Peng et al.   |         |
| 2003/0149283 | A1 |   | 8/2003  | Manzer     |         |
| 2008/0214880 | A1 |   | 9/2008  | Dubois et al. |        |
| 2009/0118549 | A1 |   | 5/2009  | Matsunami et al. |     |

FOREIGN PATENT DOCUMENTS

| DE | 850 608 C     | 9/1952  |
|----|---------------|---------|
| DE | 23 25 051 A1  | 12/1974 |
| DE | EP 0 598 228 A1 | 10/1993 |
| DE | EP 0 598 229 A1 | 10/1993 |
| DE | 42 38 493 C1  | 4/1994  |
| EP | 0509927       | 10/1992 |
| EP | 1 044 949 A1  | 10/2000 |
| FR | 695 931 A     | 12/1930 |
| FR | 846063        | 9/1939  |
| FR | 2884818       | 10/2006 |
| GB | 2 093 060 A   | 8/1982  |
| JP | 60 096513     | 5/1985  |
| JP | 2005213225    | 8/2005  |
| WO | WO 93/05006   | 3/1993  |
| WO | WO 99/05085   | 2/1999  |
| WO | WO 2006/087083 A2 | 8/2006 |
| WO | WO 2006/114506 A | 11/2006 |
| WO | WO 2007/058221 A1 | 5/2007 |
| WO | WO 2008/052993 A2 | 5/2008 |
| WO | WO 2009/029541 A1 | 3/2009 |
| WO | 2008/074090   | 5/2009  |

OTHER PUBLICATIONS

Erlenmeyer et al., "Die Dissociation des Glycerins" Annalen Der Chemie, 1904, pgs. 209-223.
Adkins et al., "Acrolein":Organic Syntheses, vol. 1 p. 6 1926, vol. 1 p. 15 1941, 4 pages.
Anon., "Modeling the reaction behavior of glycerol in sub- and supercritical water", Germany, 2000, 2 pgs.
Antal, Jr et al., "Heterolysis and Homolysis in Supercritical Water" American Chemical Society, 1985, pp. 78-87.
Barrault et al., "Selective Esterification . . . ", Chemical Industries, 1998, pp. 13-23.
Clacens et al. "Selective etherification of glycerol to polyglycerols . . . ", Applied Catalysis, 2002, pp. 181-190.
Cottin et al. "Preparation de diglycerol et triglycerol . . . ", Fondmental, Oct. 1998, pp. 407-412.
Delaby, "Academie Des Sciences" Comptes Rendus, 1923, pp. 690-693.
Hanyu et al., "Manfacture of Acrolein", Journal of the Osciety of Chemical Industry, Japan, vol. 37 1934, p. 538.
Hauschild et al. "Contribution a l'etude de la deshydratation . . . ", Bulletin de la Societe Chimique de France, 1956, pp. 878-881.
Ishikawa et al., "Generation of Trace Amount of Acrolein Standard . . . ", Bunseki Kagaku, The Japan Society for Analytical Chemistry, vol. 32 Oct. 1983, pp. E321-E325.

(Continued)

*Primary Examiner*—Sikarl A Witherspoon
(74) *Attorney, Agent, or Firm*—Wells St. John P.S.

(57) ABSTRACT

Chemical production processes are provided that can include exposing a reactant composition to a catalyst composition to form a product composition. The reactant composition can include a multihydric alcohol compound and the product composition can include a carbonyl compound. The catalyst composition can include a metal effective to facilitate catalyst activation. Processes disclosed also include supplementing a dehydration catalyst with a promoter, and activating the supplemented catalyst in the presence of oxygen. Processes also include providing a supplemented dehydration catalyst to within a reactor, and exposing a multihydric alcohol compound to the dehydration catalyst, with the exposing forming coke within the reactor. Oxygen can be provided to the reactor to remove at least a portion of the coke.

12 Claims, 5 Drawing Sheets

OTHER PUBLICATIONS

Krammer et al., "Untersuchungen zum Synthese-potential . . . ", Chemie Ingenieur Technik, 1998, pp. 1559-1563.

Moureu et al., "Memoires et Communications", Comptes Rendus, 1919, pp. 885-889.

Ott et al., "Catalytic dehydration of glycerol . . . ", The Royal Society of Chemistry, 2006, pp. 214-220.

Ott et al., Chemie Ingenieur Technik, 2004, p. 1292.

Ramayya et al., "Acid-catalysed dehydration of alcohols in supercritical water", Fuel, Oct. 1987, vol. 66, pp. 1364-1371.

Rosenthaler, L., "Beitrage zum Nachnveis organischer Verbindungen", Pharmazeutische Zeitung-Nachrichten, 1954, pp. 464-466.

Sabatier et al., "Conformement a Une Decision De L'Accademie" Comptes Rendus, 1918, pp. 1003-1039.

Waldmann et al., "Uber die Dehydratisierung . . . "Chemische Berichte, 1950, pp. 287-291.

Zhukov et al., "Definition of an Effective Catalyst in the Condensation of Glycerol", Applied Chemistry of USSR, Apr. 1980, pp. 780-783.

Corma et al. Jour of Catalysis 247 (2007) 307-27.

Ott et al., "Catalytic dehydration of glycerol . . . ", Green Chem., 2006, 8, 214-220.

Tsukuda et al. CatComm 8 (2007) 1349-1353.

PCT/US08/074094, date Feb. 5, 2009, Written Opinion.

PCT/US08/074094, date Feb. 5, 2009, Search Report.

Chai et al, "Sustainable production of acrolein: Gas-phase dehydration of glycerol over Nb2O5 catalyst" Journal of Catalysis, Academic Press, Duluth, MN, US, vol. 250, No. 2, Aug. 14, 2007, pp. 342-349, XP022200532.

Faro, A.C. et al, "Cumene hydrocracking and tiophene HDS on niobia-supported Ni, Mo and Ni-Mo catalysts" Catalysis Today, vol. 118, 2006, pp. 402-409, XP002511927.

Mishra, T. et al, "Transition metal promoted AlPO4 catalyst 2. The catalytic activity of M0.05Al0.95PO4 for alchohol conversion adn cumene cracking/dehydrogenation reactions" Applied Catalysis A: General, vol. 166, 1998, pp. 115-122, XP002511925.

Song, L. et al, "A new route to prepare supported nickel phosphide/silica-alumina hydrotreating catalysts from amorphous alloys" Catalysis Today, vol. 125, Apr. 8, 2007, pp. 137-142, XP002511926.

Tsukuda et al, "Production of acrolein from glycerol over silica-supported heteropoly acids" Jul. 21, 2007, Catalysis Communications, Elsevier Science, Amsterdam, NL, pp. 1349-1353, XP022162877.

PCT/US2008/074084, Search Report, date Oct. 21, 2009, Battelle Memorial Institute.

PCT/US2008/074084, Written Opinion, date Oct. 21, 2009, Battelle Memorial Institute.

PCT/US08/074079, Partial Search, date Mar. 9, 2009, Battelle Memorial Institute.

PCT/US08/074084, Partial Search, date May 20, 2009, Battelle Memorial Institute.

PCT/US2008/074090, Search, date Jul. 28, 2009, Battelle Memorial Institute.

PCT/US2008/074090, Writ Opin, date Jul. 28, 2009, Battelle Memorial Institute.

Database CA, Xu, Bo-Qing et al: "Process for dehydration of polyhydric alcohols" (XP-002524780), Nippon Shokubai Co., Ltd., Japan (Chemical Abstracts Service, Columbus, OH), May 24, 2007.

PCT/US2008/074079 IPRP, date Feb. 24, 2010, Battelle Memorial Institute.

PCT/US2008/074084 IPRP, date Feb. 24, 2010, Battelle Memorial Institute.

PCT/US2008/074090 IPRP, date Feb. 24, 2010, Battelle Memorial Institute.

PCT/US2008/074094 IPRP, date Feb. 24, 2010, Battelle Memorial Institute.

* cited by examiner

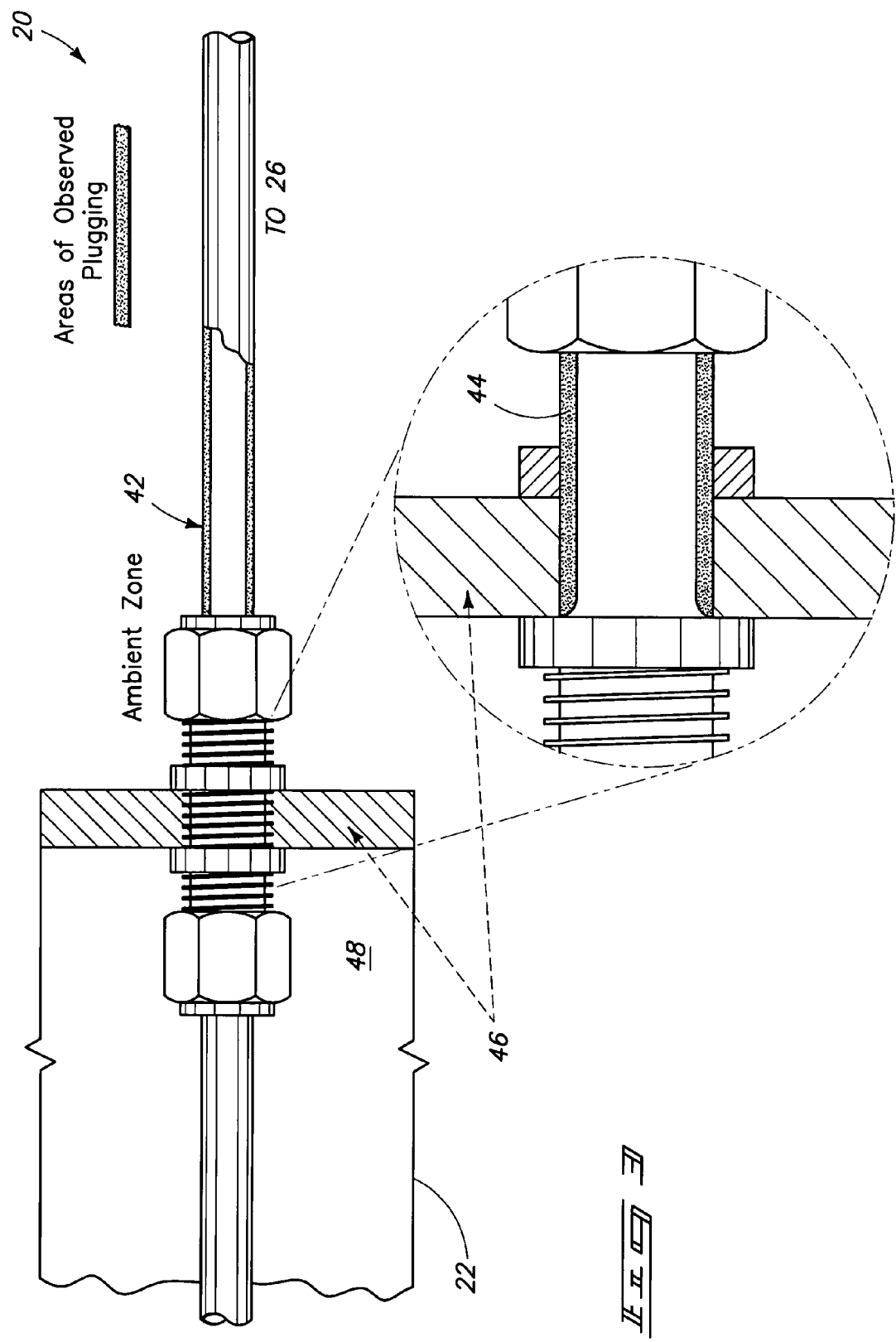

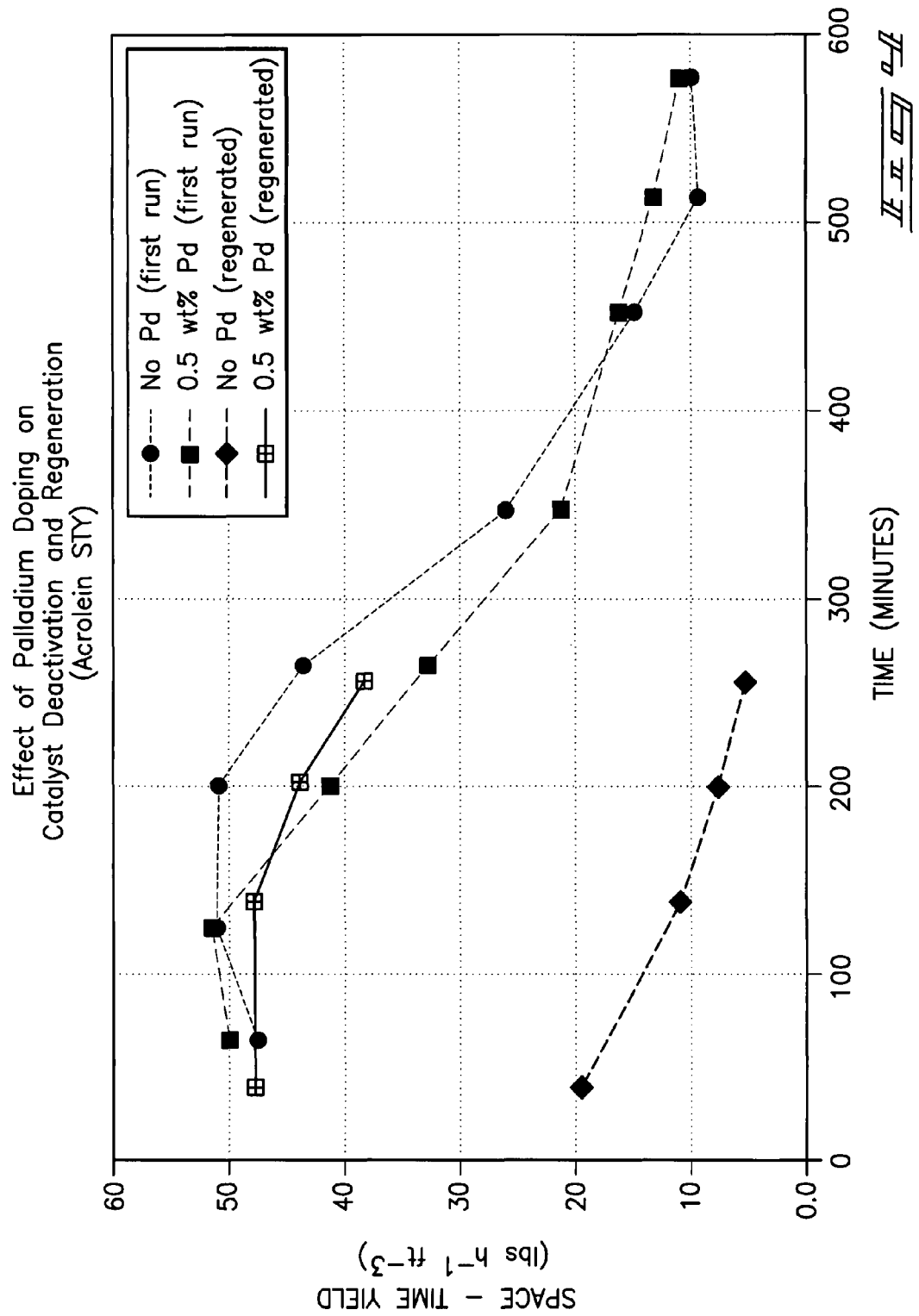

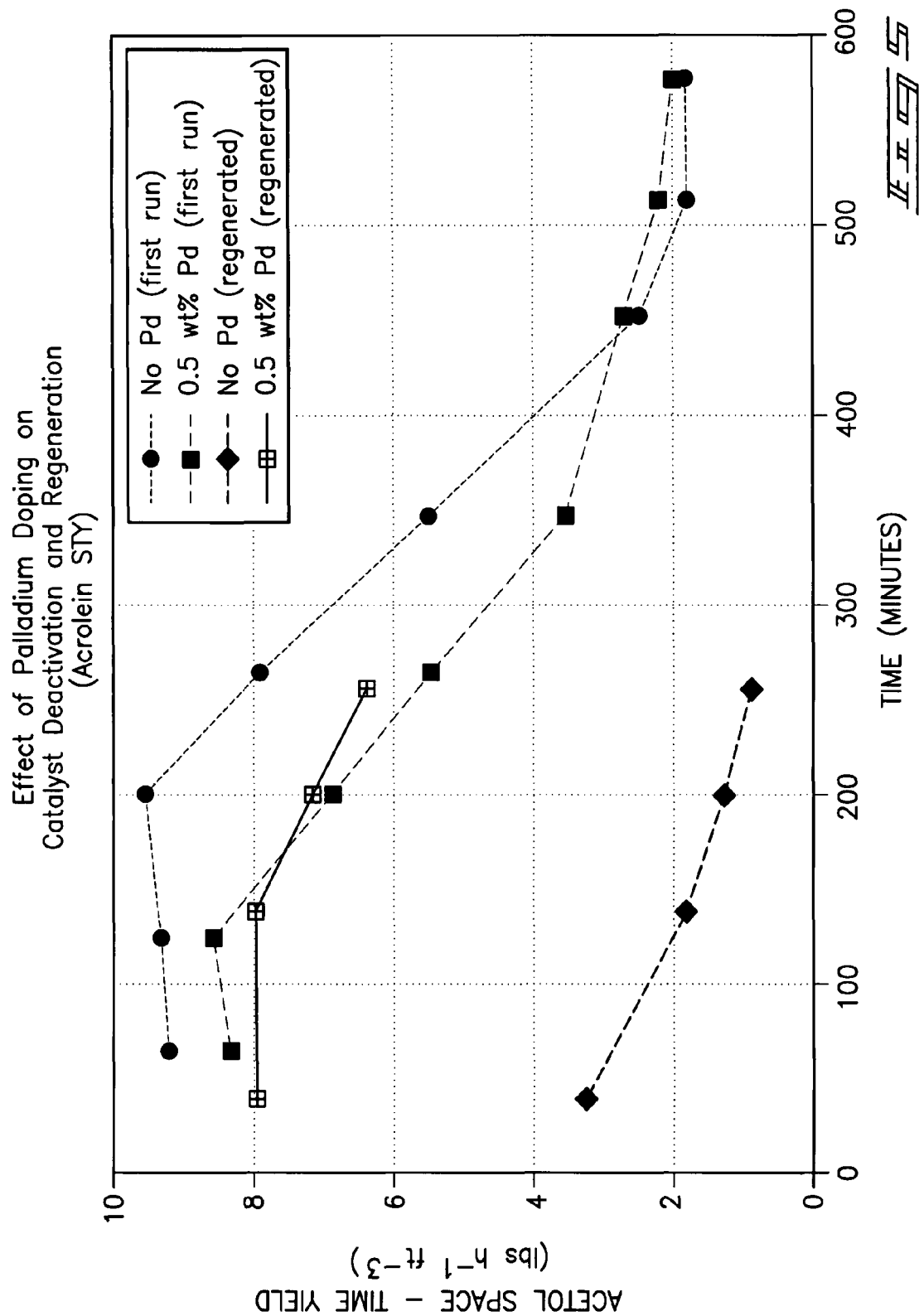

CHEMICAL PRODUCTION PROCESSES, SYSTEMS, AND CATALYST COMPOSITIONS

RELATED PATENT DATA

This application is a continuation in part of U.S. patent applications: Ser. No. 11,895,362, entitled Chemical Production Processes, Systems, and Catalyst Compositions by Peterson et al. which was filed on Aug. 24, 2007; Ser. No. 11,895,593, entitled Chemical Production Processes, Systems, and Catalyst Compositions by Peterson et al. which was filed on Aug. 24, 2007; Ser. No. 11,895,592, entitled Chemical Production Processes, Systems, and Catalyst Compositions by Peterson et al. which was filed on Aug. 24, 2007; the entirety of all are incorporated by reference herein.

TECHNICAL FIELD

The present disclosure relates to chemical production processes, systems, and catalyst compositions.

BACKGROUND OF THE DISCLOSURE

Chemical production process development can lead to the discovery of process parameters such as by-products that were previously unknown in the art. These previously unknown process parameters may limit the efficiency of the process being developed. The present disclosure provides processes, systems, and catalysts, embodiments of which, can overcome a previously unknown limiting process parameters.

SUMMARY OF THE DISCLOSURE

Chemical production processes are provided that can include exposing a reactant composition to a catalyst composition to form a product composition. The reactant composition can include a multihydric alcohol compound and the product composition can include a carbonyl compound. The catalyst composition can include a metal effective to facilitate catalyst activation.

Processes disclosed also include supplementing a dehydration catalyst with a promoter, and activating the supplemented catalyst in the presence of oxygen.

Processes also include providing a supplemented dehydration catalyst to within a reactor, and exposing a multihydric alcohol compound to the dehydration catalyst, with the exposing forming coke within the reactor. Oxygen can be provided to the reactor to remove at least a portion of the coke.

Dehydration catalysts are also provided that can include one or more elements from group 10 of the periodic table of elements.

Chemical production systems are provided that can include a reactant reservoir coupled to a reactor with the reactor containing a catalyst having one or more elements from group 10 of the periodic table of elements.

BRIEF DESCRIPTION OF THE DRAWINGS

Preferred embodiments of the disclosure are described below with reference to the following accompanying drawings.

FIG. 3 is a portion of a chemical production system according to an embodiment of the disclosure.

FIG. 4 is a plot of data acquired utilizing an embodiment of the disclosure.

FIG. 5 is a plot of data acquired utilizing an embodiment of the disclosure.

DETAILED DESCRIPTION OF THE PREFERRED EMBODIMENTS

This disclosure is submitted in furtherance of the constitutional purposes of the U.S. Patent Laws "to promote the progress of science and useful arts" (Article 1, Section 8).

Figure 1:
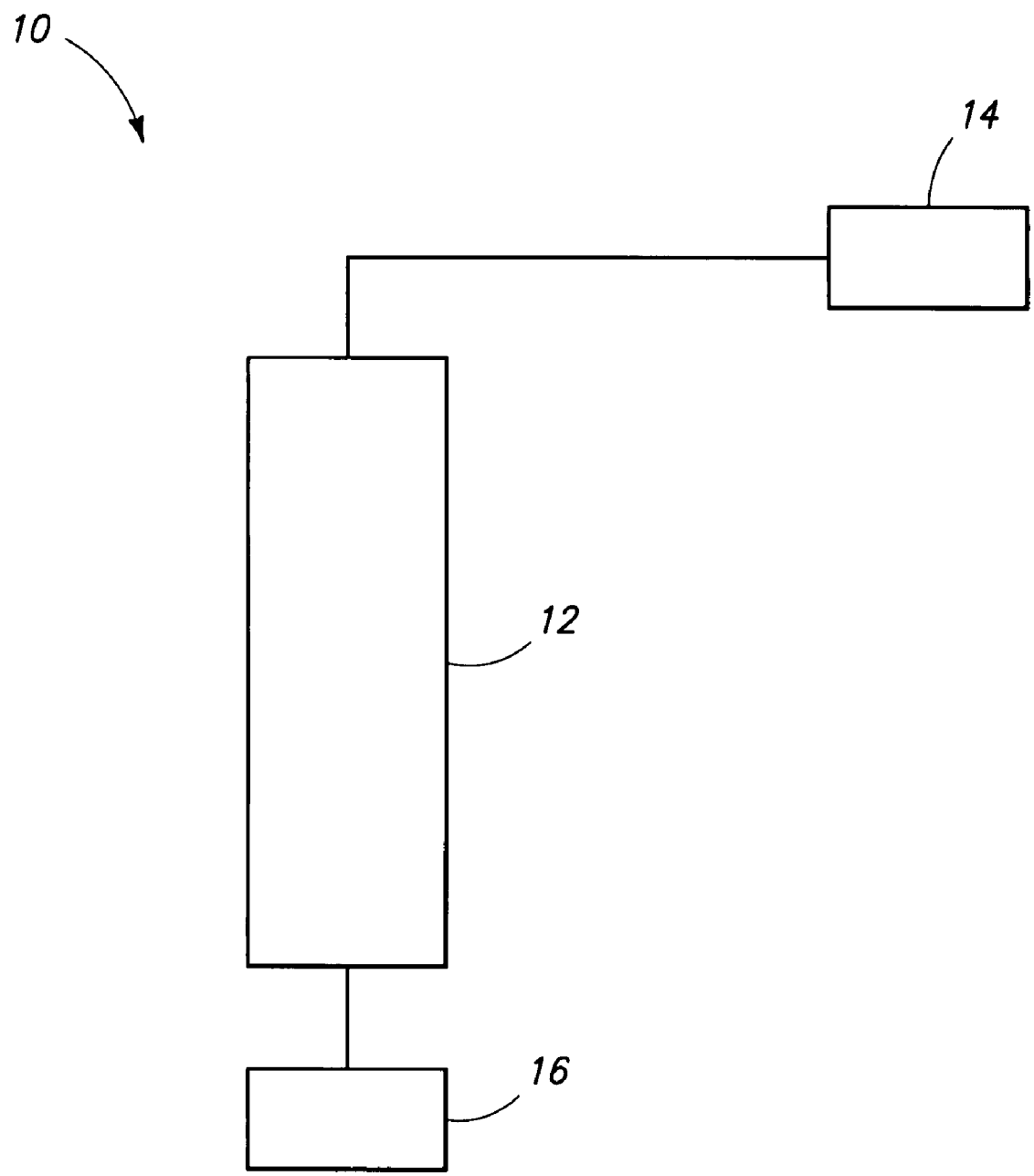
FIG. 1 is a chemical production system according to an embodiment of the disclosure.

The chemical production processes of the present disclosure will be described with reference to FIGS. 1-5. Referring first to FIG. 1, a chemical production process system 10 is shown that includes a reactor 12 coupled to both a reactant reservoir 14 and a product reservoir 16. In accordance with the present disclosure, reactant reservoir 14 can be coupled to reactor 12 utilizing conduits that facilitate the flow of reactant from reactant reservoir 14 to reactor 12. This flow can be facilitated utilizing pressure differentials between reactant reservoir 14 and reactor 12. For example, these pressure differentials can be facilitated utilizing pumps to provide a pressure differential between reactant reservoir 14 and reactor 12. The reactant within reactant reservoir 14 can be a hydroxyl compound and/or a multihydric alcohol compound. An example multihydric alcohol compound can include the compound glycerol, which when dehydrated can result in a product composition that includes one or both of acrolein and/or acetol, for example.

Reactor 12 can include a housing that can be configured to house a catalyst and be utilized to facilitate the exposure of the reactant within reactant reservoir 14 to catalyst within reactor 12. The catalyst can be a dehydration catalyst and the catalyst can be supported and/or unsupported catalyst, for example. Unsupported catalysts can be referred to as bulk catalysts. Reactor 12 can be jacketed or can be configured as a fluidized bed reactor, for example. Reactant and catalyst within reactor 12 can be configured to perform a dehydration reaction such as the dehydration of the multihydric compound glycerol to a product composition that can include one or both of acrolein and/or acetol, for example.

The product composition provided to product reservoir 16 can be a dehydration product of the multihydric alcohol compound such as a carbonyl compound. The pressure differential apparatus used to facilitate the transfer of reactant from reactant reservoir 14 can also be utilized to provide product from reactor 12 to product reservoir 16. In accordance with an example embodiment, system 10 can be configured to expose a multihydric alcohol compound such as glycerol from reservoir 14 to a catalyst composition within reactor 12 to form a product composition including one or both of acrolein and acetol.

Figure 2:
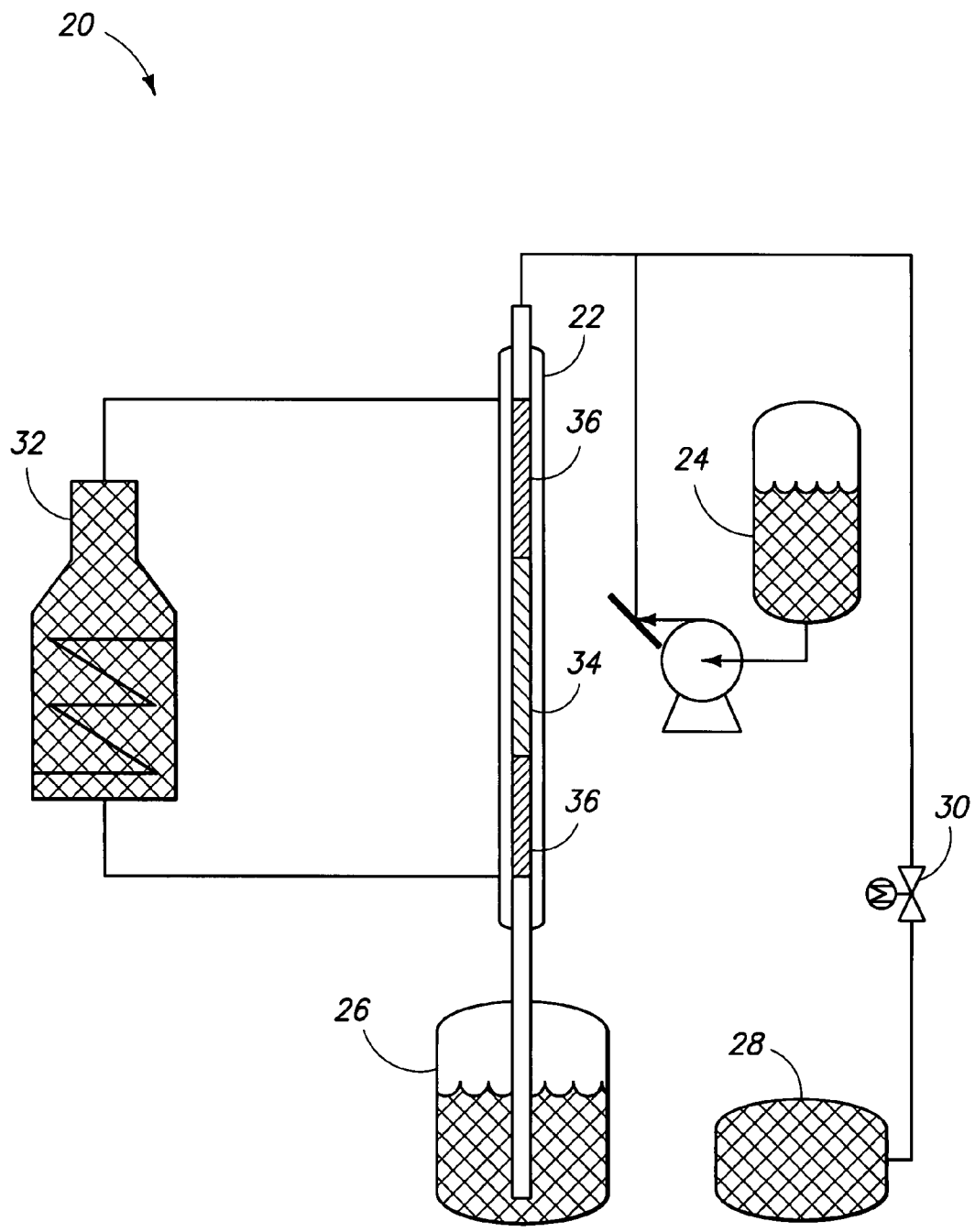
FIG. 2 is a chemical production system according to another embodiment of the disclosure.

In accordance with another embodiment, FIG. 2 depicts a chemical production system 20 that includes a reactor 22 coupled to a reactant reservoir 24 as well as a product reservoir 26. Reactant of reactant reservoir 24 can be a multihydric alcohol compound, for example. To facilitate the flow of reactant from reactant reservoir 24 to reactor 22, a carrier composition 28 including a gas or liquid such as nitrogen is provided to a reactant reservoir conduit utilizing flow control 30. In accordance with another embodiment $CO_2$ can be utilized as the carrier composition 28. These solid support beds were also treated with $CO_2$ and reactant from reactor reservoir 24 can be combined with carrier composition 28 and provided to reactor 22.

Reactor 22 can be configured as an oil heated reactor utilizing an oil heater 32. Reactor 22 can be configured having a catalyst 34 supported by packing material 36.

Catalyst 34 can be a dehydration catalyst and/or can include a metal effective to facilitate catalyst activation. The metal can include one or more elements of group 10 of the periodic table of elements. The catalyst can include Pd, for example and it may be included to an amount of at least about 5% (wt./wt.) of the entire catalyst. Additional components of the catalyst can include, for example, a phosphate composition with the phosphate composition including one or more of Cr, Mn, Fe, Co, Ni, Zn, La, Ca, Sr, Ba, Mo, Al, B, and Ru. The catalyst can also include a metal phosphorous composition with the metal phosphorous composition comprising one or more of Si and Ti. The catalyst can also be a solid substrate including one or more of $SiO_2$, $SiO_2$—$Al_2O_3$, and $TiO_2$. As another example, the catalyst can include a solid support composition such as one or more of F—$Al_2O_3$, $ZrO_2$—$CO_2$, $SiO_2$—$Al_2O_3$—$CO_2$, $SiO_2$—$Al_2O_3$, Alundum, and Silica such as Ludox AS-30. The catalyst can also include a polyoxometallates. More particularly, catalyst 34 can include Nb, Mo, and/or W. Catalyst 34 can be hydrated or an oxide. For example, catalyst 34 can be hydrated nobia. Catalyst 34 can include tungstic acid and/or phosphotungstic acid. Catalyst 34 can include phosphomolybdic acid. Catalyst 34 can be supported with a silica support. Prior to exposing reactant to catalyst 34, catalyst 34 can be exposed to carrier composition 28 such as $CO_2$.

Referring to FIG. 3, for example, it has been observed that the reactions effective to facilitate dehydration of multihydric alcohol compounds can result in the formation of by-products within the system, and these by-products can degrade the efficiency of the chemical production process being performed within the system. FIG. 3 depicts a more detailed view of system 20 of FIG. 2, and as shown reactor 22 includes a bulkhead 48 coupled to a conduit 42. Within conduit 42, by-product 44 can be observed upon use of system 22 during dehydration processes, and the formation of by-product 44 may be significant.

As an example, dehydration processes may result in coke formation and the coking may shorten catalyst life and/or deteriorate product selectivity. This can be gleaned from the highly linear relationship between carbon balance, whose deficiencies are believed to arise from this coke formation, and acrolein selectivity when reacting the multihydric compound glycerol. The relationship may indicate that acrolein decomposition may be largely responsible for coke formation and permits the extrapolation of data to force 100% carbon balance, providing an "intrinsic" selectivity for dehydration. This intrinsic selectivity essentially can describes a 2-hydroxyl elimination and to produce the 3-hydroxypropanal over 1-hydroxyl elimination to produce acetol.

Furthermore, during most reactions exhibiting sufficient catalytic activity, coke can eventually form on the exit lines of the reactor. This can lead to a restriction in the exit line, increasing pressure (and residence time) and can eventually lead to a complete plug. While the recovered catalyst from a successful test can often be grayed or blackened, the transfer lines between the exit of the reactor and the bulkhead out of the sand bath rarely showed any particulate, plug, or restriction. The coke could form almost exclusively in the bulkhead fitting or in the lines immediately following the bulkhead into the ambient temperature zone. Example chemical production processes are provided that can reduce coking and facilitate catalyst regeneration.

While coking of the system can cause difficulty during the operation of the process for extended periods, mechanical changes such as increasing the bulkhead fitting size by a factor of 2 may be utilized. For example a ⅛" bulkhead fitting can reduce the number of plugs at this location and the ¼" fitting can almost eliminate them. However, this can result in a larger number of plugs found in the transfer lines just outside of the bulkhead. This can be addressed operationally by sometimes replacing with fresh transfer lines in the middle of a process run, but this may not address the root cause.

For example, dehydration catalysts such as two Co-phosphate catalysts can be prepared with one supplemented with about 0.5% (wt./wt.) of a promoter such as Pd, then each utilized to facilitate the dehydration of the multihydric compound glycerol. To prepare the supplemented catalyst, in a jar with a stir bar can be placed 21.86 g of 25% (wt./wt.) ammonium phosphate solution. Cobalt nitrate (5.97 g) and 388 mg of palladium nitrate solution (19% (wt./wt.) Pd) can be dissolved in approximately 20 mL of deionized water. The ammonium phosphate solution can be stirred rapidly and a solution of Ludox AS-40 (25 g) and the Co/Pd solution can be added together resulting in the precipitation of a blue solid. Stirring can be continued overnight during which the color can change to pink-red. The slurry can be transferred to a 500 mL RBF and the volatile materials can be removed on a rotary evaporator (40 torr, bath temp=70° C.). The dried red-purple solid can be placed in a porcelain crucible and calcined at 350° C. for 6 hours to give a blue-gray solid. The solid can then be crushed and screened to 16-40 mesh for evaluation.

After 10 hours of continuous operation as during the dehydration of glycerol, the catalysts can be found to have performed similarly with respect to activity and selectivity over time with coking of both catalysts being observed leading to loss of about 80% of the original catalytic activity. The catalyst can then be regenerated by exposing each to air at 500° C. overnight. While both catalysts returned from their spent black color to their original blue color upon heating in the presence of air, when the catalysts are repacked into their reactors, the catalyst lacking palladium can be found to have regained less than 50% of its original activity with the Pd-supplemented catalyst returning to full activity and performing in subsequent hydrogenation reactions as it had in the original reaction. It can appear as though the metal effective to facilitate catalyst activation does not appear to alter the characteristics (activity, selectivity or lifetime), the metal/promoter improves catalyst regenerability. Data demonstrating this is shown in FIGS. 4 and 5.

The qualitative and quantitative data of FIGS. 4 and 5 can be acquired utilizing gas and liquid chromatography techniques. For example, gas chromatographic analyses can be performed utilizing a Shimadzu GC-2010 Gas Chromatograph (GC) equipped with a Flame Ionization Detection (FID) operating at 280° C., and an AOC-20 autosampler, and employing GC Solutions Software. A DB-WAX (J & W Scientific) capillary column (30 m×0.32 mm I.D.×0.25 µm film thickness) can be employed utilizing helium as carrier gas at a 2.61 mL/min flow rate. Injections of 1 µL utilizing a 25:1 split ratio can be made with the injector port maintained at 250° C. Oven temperature programming can utilize an initial temperature of 40° C. with a hold for 5 minutes followed by a 10° C./min ramp to 245° C. and a hold at the final temperature for 4.5 minutes. Calibrations can be performed on a monthly basis using known standard solutions for glycerol, acrolein, and acetol. Calibrations can take place using a series of five standard solutions prepared by serial dilution to determine the linear response for each compound, and acceptance of each curve determined if the linear response had an R value of greater than 0.99.

Liquid chromatographic analyses can be carried out on a Waters LC system incorporating a Waters 515 pump, Waters 2410 Refractive Index Detector (RID), and a Waters 717plus Autosampler for sample introduction. Analyses can be performed utilizing Empower Pro Software. Separations of 10 µL injections can be effected on an Aminex HPX-87H Organic Acid Analysis column operated at 35° C. and employing a 0.005M $H_2SO_4$ as the eluent with a flow rate of 0.55 mL/min. Total run times of 45 minutes were sufficient to elute all compounds of interest. Calibration curves can be prepared as described for GC calibrations and using the same set of standard solutions used for GC calibration.

Referring to product reservoir 26 of system 20, upon exiting reactor 22, product can be acquired by time collection of reactor 22 effluent in a known quantity of a chilled scrub solution containing 1 wt % n-BuOH with mass balances for a given reactor run determined by a ratio of collected effluent mass to expected mass based on feed rate and run time. For example, two small aliquots can be removed and diluted to concentrations appropriate for GC and LC analyses. The diluted samples can then be analyzed as described previously and wt % compositions determined from calibrated detector responses used to determine absolute compositions of the collected effluent. The use of known quantities of n-BuOH in the scrub solutions can permit a primary check of analytical sampling technique, but was not used as an internal standard by which response factors for effluent components were measured. Reported values for conversion, yield, selectivity, and carbon balance present averages of those values determined by both GC and LC analyses. Glycerol conversion can be calculated by the differences between calculated quantity of glycerol feed (based on feed rate and run time) and the quantity of glycerol collected in the reactor effluent and may be uncertain when mass balances are not satisfactory. Values exclude any experimental runs that did not provide mass balances in excess of 90%. Product yields can be calculated by the ratio of quantity of product formed to the quantity of glycerol. Field product selectivities can be calculated from the quantity of product formed divided by the quantity of glycerol converted. Carbon balances can be calculated from the sum of the molar quantities of glycerol, acrolein, and acetol components divided by the molar quantity of glycerol fed. Liquid Chromatographic techniques can permit the quantification of formic acid and acetic acid by-products. However, since their combined quantity rarely exceeded 3%, their presence was not included in carbon balance determination.

As the examples illustrate, when the dehydration reaction is conducted with fresh catalyst without palladium doping, acrolein contact time yields of approximately 50 lbs ft$^3$ h$^{-1}$ can be realized initially, dropping to half that value within 5 hours of continuous operation and experiencing a further reduction after an additional 5 hours of running. Acetol contact time yields demonstrated quantitatively the same behavior exhibiting half lives of approximately 5 hours. The catalyst containing 0.5% (wt./wt.) Pd can exhibit identical behavior with respect to both acrolein and acetol contact time yields. The catalysts can be removed and regenerated at 500° C. in the presence of supplied air. The catalyst lacking Pd supplement can regain less than half of its original activity, losing half of its activity after 4 hours of operation. In contrast, the Pd-supplemented catalyst can be returned to its original productivities for both acetol and acrolein and can behave similarly to fresh catalysts in 4 hours of operation.

Utilization of a promoter can allow for catalytic glycerol dehydration technology that would otherwise be nonviable due to short catalyst lifetimes by facilitating catalyst regeneration in air, a practice particularly amenable to moving or fluidized bed reactor operations. The published literature describing catalytic glycerol dehydration does not mention coking as reason for catalyst deactivation. Consequently, published literature is devoid of any solution to the problem of deactivation by coke. As such, a method to prepare catalysts with long duty times is useful and constitutes platforms for strong catalysts.

In compliance with the statute, this disclosure has been provided in language more or less specific as to structural and methodical features. It is to be understood, however, that the disclosure is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A chemical production process comprising:
   providing a supplemented dehydration catalyst to within a reactor, the supplemented dehydration catalyst comprising at least one element of group 10 of the periodic table of elements;
   exposing a multihydric alcohol compound to the dehydration catalyst, the exposing producing a dehydration product of the multihydric alcohol compound, and forming coke within the reactor; and
   providing oxygen to the reactor to remove at least a portion of the coke.

2. The chemical production process of claim 1 wherein the supplemented catalyst comprises both an element from group 10 of the periodic table and an element from group 5 or 6 of the periodic table.

3. The chemical production process of claim 1 wherein a portion of the interior volume of the reactor is heated to at least about 500° C.

4. A chemical production system comprising a reactant reservoir coupled to a reactor, the reactor containing a catalyst comprising both one or more elements from group 10 of the periodic table of elements, and a phosphate composition, the phosphate composition comprising one or more of Cr, Mn, Fe, Co, Ni, Zn, La, Ca, Sr, Ba, Mo, and Ru, wherein the reactant reservoir contains a multihydric alcohol compound.

5. The system of claim 4 wherein the catalyst composition comprises Pd.

6. The system of claim 4 wherein the catalyst composition comprises at least 5% (wt./wt.) of the one or more elements.

7. The system of claim 4 wherein the catalyst composition comprises a solid substrate comprising one or more of $SiO_2$, $SiO_2$—$Al_2O_3$, and $TiO_2$.

8. The system of claim 4 wherein the catalyst composition comprises a solid support composition, the solid support composition comprising one or more of F—$Al_2O_3$, $ZrO_2$—$CO_2$, $SiO_2$—$Al_2O_3$—$CO_2$, $SiO_2$—$Al_2O_3$, and Alundum.

9. The system of claim 4 wherein the catalyst composition further comprises one or more of Nb, Mo, and W.

10. The system of claim 4 wherein the catalyst composition further comprises one or more of niobia, hydrated niobia, tungstic acid, phosphotungstic acid, and phosphomolybdic acid.

11. The catalyst of claim 1 wherein the multihydric alcohol compound is glycerol and the dehydration product of the multihydric alcohol compound is one or both of acetol and acrolein.

12. The system of claim 4 wherein the multihydric alcohol compound is glycerol.

* * * * *

UNITED STATES PATENT AND TRADEMARK OFFICE
CERTIFICATE OF CORRECTION

PATENT NO. : 7,872,158 B2
APPLICATION NO. : 11/895414
DATED : January 18, 2011
INVENTOR(S) : Thomas H. Peterson et al.

It is certified that error appears in the above-identified patent and that said Letters Patent is hereby corrected as shown below:

On the Title page

Item (56) References Cited – Replace "Hanyu et al., "Manfacture of Acrolein", Journal of the Osciety of Chemical Industry, Japan, vol. 37 1934, p. 538." with --Hanyu et al., "Manufacture of Acrolein", Journal of the Society of Chemical Industry, Japan, vol. 37, 1934, p. 538.--

Item (56) References Cited – Replace "Mishra, T. et al, Transition metal promoted A1P04 catalyst 2. The catalytic activity of M0.05A10.95P04 for alchohol conversion adn cumene cracking/dehydrogenation reactions" Applied Catalysis A: General, vol. 166, 1998, pp. 115-122, XP002511925." with --Mishra, T. et al., Transition metal promoted A1P04 catalyst 2. The catalytic activity of M0.05A10.95P04 for alcohol conversion and cumene cracking/dehydrogenation reactions", Applied Catalysis A: General, Vol. 166, 1998, pp. 115-122, XP002511925.--

Signed and Sealed this
Seventeenth Day of July, 2012

David J. Kappos
*Director of the United States Patent and Trademark Office*